United States Patent [19]

Patnaik

[11] Patent Number: 5,728,751
[45] Date of Patent: Mar. 17, 1998

[54] BONDING BIO-ACTIVE MATERIALS TO SUBSTRATE SURFACES

[75] Inventor: Birendra K. Patnaik, Chester, N.J.

[73] Assignee: Meadox Medicals, Inc., Oakland, N.J.

[21] Appl. No.: 755,187

[22] Filed: Nov. 25, 1996

[51] Int. Cl.⁶ .......................... C08H 1/00; C08B 37/10; A61F 2/06
[52] U.S. Cl. .......................... 523/112; 525/54.2; 623/1; 623/4; 623/5; 623/6; 623/8; 623/11; 623/12; 604/266
[58] Field of Search .......................... 525/54.2; 523/112; 623/1, 4, 5, 6, 8, 11, 12; 604/266

[56] References Cited

U.S. PATENT DOCUMENTS

| | | | |
|---|---|---|---|
| 4,229,838 | 10/1980 | Mano | 3/1.4 |
| 4,331,697 | 5/1982 | Kudo et al. | 427/2 |
| 4,521,564 | 6/1985 | Solomon et al. | 525/54.1 |
| 4,613,517 | 9/1986 | Williams et al. | 427/2 |
| 4,642,242 | 2/1987 | Solomon et al. | 427/2 |
| 4,678,660 | 7/1987 | McGary et al. | 424/25 |
| 4,713,402 | 12/1987 | Solomon | 523/112 |
| 4,720,512 | 1/1988 | Hu et al. | 523/112 |
| 4,786,556 | 11/1988 | Hu et al. | 428/412 |
| 4,973,493 | 11/1990 | Guire | 427/2 |
| 4,979,959 | 12/1990 | Guire | 623/66 |
| 5,061,777 | 10/1991 | Yoda e al. | 528/61 |
| 5,077,352 | 12/1991 | Elton | 525/409 |
| 5,077,372 | 12/1991 | Hu et al. | 528/70 |
| 5,132,108 | 7/1992 | Narayanan et al. | 424/78.17 |
| 5,134,192 | 7/1992 | Feijen et al. | 525/54.1 |
| 5,258,041 | 11/1993 | Guire et al. | 623/66 |
| 5,409,696 | 4/1995 | Narayanan et al. | 424/78.17 |
| 5,451,424 | 9/1995 | Solomon et al. | 427/2.1 |

OTHER PUBLICATIONS

Byun et al, "Heparin Surface Immobilization through Hyrophilic Spacers: Thrombin and Antithrombin III Binding Kinetics", J. Biomater. Sci. Polymer Edn, vol. 6, No. 1, pp. 1–13, 1994.

Heparin Immobilization Onto Segmented Polyurethaneurea Surfaces–Effect of Hydrophilic Spacers, by Ki Dong Park, Teruo Okano, Chisato Nojiri, and Sung Wan Kim, Journal of Biomedical Materials Research, vol. 22, 977–992 (1988).

SPUU–PEO–Heparin Graft Copolymer Surfaces: Patentcy and Platelet Deposition in Canine Small Diameter Arterial Grafts by Won Gon Kim, Ki Dong Park, Syed F. Mohammad and Sung Wan Kim; ASAIO Trans 37: M148–M149 (1991).

Synthesis and Characterization of SPUU–PEO–Heparin Graft Copolymers, by Ki Dong Park, Al Zhi Piao, Harvey Jacobs, Teruo Okano and Sung Wan Dim, Journal of Polymer Science: Part A: Polymer Chemistry; vol. 29, 1725–1737 (1991).

PEO–Modified Surfaces–In Vitro, Ex Vivo, and In Vivo Blood Compatibility by Ki Dong Park and Sung Wan Kim in Poly(Ethylene Glycol) Chemistry: Biotechnical and Biomedical Applications, 283–301 (1992).

In Vivo Nonthrombogenicity of Heparin Immobilized Polymer Surfaces by Chisato Nojiri, Ki Dong Park, David W. Grainger, Harvey A. Jacobs, Teruo Okano, Hitoshi Koyanagi and Sung Wan Kim; ASAIO Trans 36: M168–M172 (1990).

*Primary Examiner*—Frederick Krass
*Attorney, Agent, or Firm*—Hoffman & Baron, LLP

[57] ABSTRACT

A medical device having a bio-active coating is prepared by providing a polymeric substrate having hydroxyl and/or amine functionality on a surface thereof and applying the bio-active coating to the surface. The bio-active coating is the reaction product of two different reactions. The first reaction includes reacting the polymeric substrate with a hydrophilic, isocyanate-terminated spacer having at least one isocyanate group at its first and second ends. The second reaction includes reacting a remaining, unreacted isocyanate-terminated end of the spacer with a bio-active agent to bond the bio-active agent to the spacer.

28 Claims, No Drawings

BONDING BIO-ACTIVE MATERIALS TO SUBSTRATE SURFACES

FIELD OF INVENTION

The present invention relates generally to medical devices having bio-active polymer coatings. More particularly, the present invention relates to medical devices having polymeric substrate surfaces which are treated with improved bio-active polymeric coating compositions that are attached to the substrate via hydrophilic, isocyanate-terminated spacer groups which are covalently bonded to bio-active agents. Also provided are methods for preparing the same.

BACKGROUND OF THE INVENTION

It is well known to use bio-active materials to coat structures to be introduced into a living system. Over the last 30 years, research into this area has become increasingly important with the development of various bio-compatible substrates for use in contact with blood, such as, for example, vascular grafts, artificial organs, endoscopes, cannulas, and the like.

While various materials have been used to make such substrates, synthetic polymers have been increasingly popular as the preferred materials due to their anti-thrombogenic and good mechanical properties. For example, polyurethane is a useful and effective material with a variety of clinical applications. Although synthetic polymers, such as PTFE and polyurethane, are less thrombogenic than earlier materials, thrombus formation is still a problem. A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. Thus, thrombus formation is a serious complication in surgery and clinical application of artificial organs.

Various anti-thrombogenic agents, such as, heparin, have been developed and incorporated into bio-compatible substrates to combat thrombus formation. In a living system, heparin inhibits the conversion of a pro-enzyme (prothrombin) to its active form (thrombin). Thrombin catalyzes a complicated biochemical cascade which ultimately leads to the formation of a thrombus.

Infection is also a serious concern for substrates to be implanted into a host organism. Bacterial, viral and other forms of infection may lead to life-threatening complications when a substrate is implanted into a host organism. Thus, binding of an anti-infection agent to a surface of an implantable substrate can reduce the risk of infection when a substrate is introduced into a host organism.

The art is replete with various procedures for grafting bio-active molecules onto polymer surfaces to prevent thrombus formation and/or infection. For example, bio-compatible polymer surfaces have been described with various benefits including decreased thrombogenicity, increased abrasion-resistance and improved hydrophilic lubricious properties. Alternatively, preparing polymeric surfaces to receive bio-active agents by plasma treatment is also well known in the art.

Furthermore, polymer coatings are described that include either covalently or ionically binding bio-active agents to substrate surfaces. For example, as discussed hereinbelow, photochemical reactions are described which covalently bind bio-active agents to substrate surfaces. Also, quaternary ammonium reagents are described which ionically bind a bio-active agent to a substrate.

Alternatively, various substrate surfaces have previously been described that are suitable for introducing into a biological system without pretreatment of any bio-active agent. For example, Yoda et al. in U.S. Pat. No. 5,061,777 disclose that polyurethanes and polyurethaneureas containing both hydrophilic and hydrophobic polyether segments are more anti-thrombogenic than substrates produced from either a hydrophilic or a hydrophobic polyol exclusively. Similarly, Elton in U.S. Pat. No. 5,077,352 discloses a method of forming a mixture of an isocyanate, a polyol and a poly(ethylene oxide) in a carrier liquid. This mixture is then heated and cured to form a coating of a polyurethane complexed with a poly(ethylene oxide) having good adherence to a substrate and good anti-friction properties.

A significant limitation of these bio-compatible polymer surfaces, however, is that they are not completely bio-compatible. Thrombus formation and infection continue to pose problems when a substrate is implanted within a host using these bio-compatible polymer surfaces. Thus, various alternative methods have been described for preparing the surface of a substrate to be implanted in a host organism to accept bio-active agents. Plasma treatment of substrate surfaces is one such method.

For example, Hu et al. in U.S. Pat. No. 4,720,512 disclose a method for imparting improved anti-thrombogenic activity to a polymeric support structure by coating it with an amine-rich material, e.g., a polyurethaneurea, introducing hydrophobic groups into the amine-rich surface coating through plasma treatment with fluorine compounds, and covalently bonding an anti-thrombogenic agent to the hydrophobic amine-rich surface.

Such a method for plasma treating a substrate surface is limited in its scope because it only works with certain substrates. Thus, it does not provide a general purpose coating composition that can bind to a variety of substrate surfaces. In an alternate approach, however, various methods have been described for binding bio-active agents directly to substrate surfaces.

For example, Solomon et al. in U.S. Pat. No. 4,642,242 disclose a process for imparting anti-thrombogenic activity to a polyurethane polymer material by coating a support structure with a protonated amine-rich polyurethaneurea, activating the amine moiety with an alkaline buffer, and covalently linking an anti-thrombogenic agent, e.g., heparin, to the polyurethaneurea with a reducing agent.

Bio-active agents bound directly to polymer backbones suffer from several limitations. First, because these bio-active agents are directly linked to the polymer backbone, their in vivo mobility is decreased. Second, the process of linking the bio-active agent to the polymer backbone may diminish the number of functional binding sites on the bio-active agent. Third, the bio-active agent's close proximity to the polymer backbone limits its ability to interact with its physiological substrates. Thus, for all of these reasons, coatings containing bio-active molecules bound directly to the polymer backbone are limited by the bio-active agent's decreased activity.

Accordingly, alternative methods have been developed for binding bio-active molecules to substrate surfaces. In particular, methods for ionically binding bio-active agents to a substrate via a quaternary ammonium compound have been described. See for example, Mano in U.S. Pat. No. 4,229,838, Williams et al. in U.S. Pat. No. 4,613,517, McGary et al. in U.S. Pat. No. 4,678,660, Solomon et al. in U.S. Pat. No. 4,713,402, and Solomon et al. in U.S. Pat. No. 5,451,424.

These methods, however, are severely limited because the bio-active agent is leached over time from the surface of the substrate. Thus, the protection afforded by the ionically bound bio-active agent to the substrate surface is transient at best. Accordingly, more permanent methods for binding bio-active molecules to substrate surfaces have also been developed. These methods include covalently binding a bio-active molecule, either directly, or via a spacer molecule, to a substrate surface.

For example, photochemical reactions have been described for preparing substrate surfaces to receive anti-thrombogenic agents. Kudo et al. in U.S. Pat. No. 4,331,697 disclose a method for imparting anti-thrombogenic activity to a biomedical material by directly linking a heparin derivative to the surface of the material via actinic radiation. Similarly, Kudo et al. also disclose coating a surface of a biomedical material with a polymer having a carboxylic acid halide group and/or a carboxylic anhydride functional group as a side chain that can react with a heparin derivative.

Alternatively, Guire et al. in U.S. Pat. Nos. 4,973,493 and 4,979,959 disclose methods for binding bio-active molecules to substrates using a linking moiety with functionalized end groups preferably that are activated by different signals. The linking moiety can covalently bind a bio-active molecule upon introduction of a first activation signal which activates the first functionalized end group. The linking moiety is further capable of covalently binding to the substrate upon introduction of a second, different, signal (photochemical) which activates the second functionalized end group.

Bichon et al. in U.S. Pat. No. 4,987,181 disclose a substrate having an adhesive film with anti-thrombogenic properties on its surface. This adhesive film is an olefinic copolymer having side groups distributed randomly on the main chain, wherein these side groups are carboxylic groups and groups of the formula —CONH—$(CH_2)_n$—NH—$CH_2$—R, wherein R is a heparin molecule or a depolymerization fragment of a heparin molecule. The adhesive film is deposited onto the substrate via photo-initiated polymerization of a suitable monomer. Thus, heparin, or a fragment thereof, is covalently linked to the substrate via an amine spacer.

Thus, various spacer molecules that link bio-active agents to polymer substrates have been described by the above-referenced studies. These studies indicate that bio-active agents, such as, for example, heparin bound to polymer coatings, retain more of their activity if they are tethered away from the surface of a substrate by a spacer. Although spacer molecules provide a means for optimizing the bio-activity of bio-active molecules bound to substrate surfaces, several problems persist in the photochemical reactions used to bind these bio-active molecules via spacers to substrate surfaces. Included among these problems are the ability of the bio-active molecule to withstand the photochemical signal used to bind it to the substrate surface, as well as, the ability of the substrate to withstand photoradiation. For example, inert polymeric substrates, e.g., polytetrafluoroethylene, degrade when exposed to photochemical reactions and cannot be used therewith. Thus, attempts have been made to use spacer molecules to bind bio-active agents to substrate surfaces without photochemical reactive groups.

For example, in a process developed by Park et al. for coating glass beads and tubing, heparin was coupled to a segmented polyetherurethaneurea (PUU) with a reaction scheme that involved coupling a diisocyanate-derivatized poly(ethylene oxide) (PEO) spacer group to a segmented PUU through an allophanate/biuret reaction. In a subsequent condensation reaction, the free isocyanate remaining on the spacer group was coupled to a functional group (—OH, —$NH_2$) on a heparin molecule.

Briefly, this process included derivatizing PEO polymers with diisocyanate functional groups by reacting toluene diisocyanate (TDI) with PEO. This reaction takes 2–3 days at 60° C. to complete. After purification, the TDI-PEO-TDI spacer groups are grafted onto the PUU backbone through an allophanate/biuret reaction between the urethane/urea-nitrogen proton and the terminal isocyanate group of the isocyanate derivatized PEO. The TDI-PEO-TDI spacers are coupled to the surface of, e.g., polymer-coated glass beads in the presence of a catalyst (0.1% (v/v) dibutyltin dilaurate in benzene).

After washing the polymer-coated beads in benzene, heparin is covalently bonded to the polymer backbone via the free isocyanate group on the PEO spacer in the presence of a catalyst (0.5% (v/v) dibutyltin dilaurate in benzene) for 3 days at room temperature. The beads were then washed in acetone and rinsed in distilled water.

Clearly, the above described process is time consuming, as well as, prone to multiple side reactions. Furthermore, the reaction product is difficult to manipulate because of its low solubility in polar solvents. Accordingly, Park et al. developed a new soluble segmented PUU-PEO-Heparin graft copolymer with improved blood compatibility.

In particular, the new soluble graft copolymer composition is derived from a four step process, wherein heparin is immobilized onto a commercial preparation of a segmented PUU using hydrophilic PEO spacers of different molecular weights. This new method includes (1) coupling hexamethyldiisocyanate (HMDI) to a segmented polyetherurethaneurea backbone through an allophanate/biuret reaction between the urethane/urea-nitrogen proton and one of the isocyanate groups on the HMDI. Next, (2) the free isocyanate groups attached to the backbone are then coupled to a terminal hydroxyl group on a PEO to form a PUU-PEO complex. Next (3) the free hydroxyl groups of the PUU-PEO complex are treated with HMDI to introduce a terminal isocyanate group. Finally, (4) the NCO functionalized PUU-PEO is then covalently bonded to reactive functional groups on heparin (—OH and —$NH_2$) producing a PUU-PEO-Hep product. K. D. Park and S. W. Kim, "PEO-Modified Surfaces—In Vitro, Ex Vivo and In Vivo Blood Compatibility", in Poly(Ethylene Glycol) Chemistry: Biotechnical and Biomedical Applications 283, 293–295 (J. Milton Harris ed. 1992). This method will be referred to hereinafter as the "Park Method."

The Park Method, however, like its predecessor, suffers from several draw backs. In particular, because of the number of reactions steps involved in the Park Method, the synthesis of the coating composition is slow, inefficient and prone to side reactions which contributes to a low yield and an increase in the amount of cross-linked polymer.

In general, all of these disclosures have addressed substrate surfaces and/or coatings therefor which can exist within biological systems and in particular, can increase the anti-thrombogenicity of the surface of, e.g., medical substrates. These reactions, however, are generally slow, multi-step syntheses, and are characterized by side reactions which lead to low yields and formation of cross-linked polymers. In addition, these reactions cannot be universally applied to substrate surfaces. Thus, in particular, there is a need for a bio-active coating and process that can be used with a broad spectrum of substrate surfaces. In addition, there is a need particularly for medical devices that utilize hydrophilic isocyanate-terminated spacers to maximize the bio-activity of the bio-active agent. There is also a need for a simplified method of preparing such bio-active coatings that provide higher yields with negligible cross-linking, in a shorter period of time. The present invention is directed toward providing solutions therefor.

SUMMARY OF THE INVENTION

The present invention relates to an implantable medical device that includes a bio-compatible polymeric substrate surface bonded to a pendant bio-active-containing moiety via the reaction of available functional groups on the substrate with the pendant bio-active-containing moiety. In this embodiment, the moiety is represented by the formula:

wherein $R^1$ is an hydrophilic spacer selected from the group consisting of aliphatic hydrocarbons, poly(oxy olefins) hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides. $R^2$ is a bio-active agent selected from the group consisting of antithrombogenic agents, antibiotics, antibacterial agents, antiviral agents, their pharmaceutical salts and mixtures thereof.

In another embodiment, the present invention relates to an implantable medical device having a bio-active coating which is prepared by providing a bio-compatible polymeric substrate having reactive functionality on its surface, such as for example hydroxyl and/or amine functionality, and applying the bio-active coating to a surface thereof. The bio-active coating is the reaction product of two different reactions. The first reaction includes reacting the bio-compatible polymeric substrate with a hydrophilic spacer having at least one reactive functional group at its first and second ends. In this reaction, one of the reactive functional groups of the spacer reacts with the reactive functionality on the substrate surface to bond the spacer to the bio-compatible polymeric substrate. The second reaction includes bonding a remaining unreacted reactive functional group on the unreacted end of the spacer with a bio-active agent to bond the bio-active agent to the spacer.

Another embodiment of the present invention relates to a method of preparing a bio-active coating. This coating includes providing a hydrophobic, bio-compatible polymeric substrate having reactive functionality on its surface, such as for example hydroxyl and/or amine functionality. The reactive functionality of the bio-compatible polymeric substrate is then reacted with a hydrophilic spacer having at least one reactive functional group at its first and second ends. In this reaction, one of the reactive functional groups on the spacer reacts with the reactive functionality on the bio-compatible polymeric substrate to bond the spacer to the substrate. A remaining unreacted functional group on the spacer is then reacted with a bio-active agent to bond the bio-active agent to the spacer.

In another embodiment, a medical device having a bio-active coating is prepared by providing a bio-compatible polymeric substrate having a reactive functionality on its surface, such as for example a hydroxyl and/or amine functionality, and applying the bio-active coating thereto. The bio-active coating is the reaction product of three different reactions. The first reaction includes reacting the bio-compatible polymeric substrate with a hydrophilic spacer having at least one reactive functional group at its first and second ends. In this reaction, one of the reactive functional groups on the spacer reacts with the reactive functionality on the bio-compatible polymeric substrate surface to bond the spacer to the bio-compatible polymeric substrate (spacer-substrate product). The second reaction includes reacting a chain extending moiety having at least one reactive functional group at is first and second ends with an unreacted end of the spacer. The third reaction includes reacting an unreacted end of the chain extending moiety with a bio-active agent to covalently bond the bio-active agent to the spacer.

DETAILED DESCRIPTION OF THE INVENTION

While this invention is satisfied by embodiments in many different forms, there will be described herein in detail preferred embodiments of the invention, with the understanding that the present disclosure is to be considered as exemplary of the principles of the invention and is nor intended to limit the invention to the embodiments illustrated and described. The scope of the invention will be measured by the appended claims and their equivalents.

In accordance with the present invention, medical devices having novel bio-active coatings are provided. More particularly, novel compositions and methods are provided for the synthesis of heparinized polyurethanes.

The bio-active coatings, medical devices and methods described herein are particularly advantageous over previously disclosed polymer coatings, especially the Park Method described hereinabove because the composition and structure of the present coatings are more controllable and reproducible. In addition, the properties of the bio-active coatings of the present invention can be varied easily, e.g., biostability, hydrophilicity etc. Also, the methods of synthesizing the present bio-active coatings are more efficient and take less time than previously disclosed methods. Another advantage of the present invention is that the reactions may be carried out at lower temperatures. Importantly, the reaction schemes of the present invention form fewer cross-links and provide higher polymer yields than previously described methods.

In one embodiment of the present invention, an implantable medical device is provided that includes a bio-compatible polymeric substrate surface bonded to a pendant bio-active-containing moiety. The moiety is bonded to the polymeric substrate via the reaction of available functional groups on the substrate surface with the moiety. An example of the moiety is represented by the following structure:

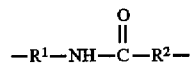

wherein $R^1$ is an hydrophilic spacer selected from the group consisting of aliphatic hydrocarbons, poly(oxy olefins), hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides; and $R^2$ is a bio-active agent selected from the group consisting of antithrombogenic agents, antibiotics, antibacterial agents, antiviral agents, their pharmaceutical salts and mixtures thereof.

In another one embodiment of the present invention, there is provided a medical device having a bio-active coating. This medical device is prepared by providing a bio-compatible polymeric substrate having reactive functionality, such as for example, hydroxyl and/or amine functionality on the surface thereof. The reactive functionality is introduced onto a surface of the bio-compatible polymeric substrate for reaction with a spacer group, such as for example, an isocyanate-terminated PEO spacer.

The reactive functionality on the surface of the substrate may be introduced thereon by conventional methods, including for example, plasma glow discharge. The reactive functionalities of the present invention may be introduced onto the surface of, for example, an implantable medical device in any form compatible with the present bio-compatible coatings, such as for example as a film or emulsion. For purposes of the present invention the reactive functionalities may be chemically or physically bonded to the surface of, e.g., a medical device.

Preferably the medical devices of the present invention are implantable within, for example, the body of a human. In its broadest terms, however, a medical device of the present invention may be any bio-compatible polymeric substrate compatible with the present bio-active coating which, absent the coating, may lead to thrombus formation and/or infection when in contact with a body tissue or fluid. The bio-compatible polymeric substrate is preferably made from hydrophobic, inert polymeric material including, for example, expanded polytetrafluoroethylene (ePTFE) and polyethyleneterephthalate (PET). Exemplary of, but not limited to, such medical devices are vascular access (arterial and venous) catheters, introducers, vascular grafts, endoprosthesis, stents, stent-graft combinations, urinary catheters and associated substrates, such as drainage bags and connectors, and all abdominal cavity drainage tubing, bags and connectors. Preferred medical devices are, for example, ePTFE vascular grafts. For purposes of this invention, "vascular grafts" is meant to include endoprostheses.

An implantable medical device of the invention was prepared by providing a bio-compatible polymeric substrate as described above, and applying a bio-active coating to the surface thereof. The bio-active coating is the reaction product of a first reaction which includes bonding available reactive functional group(s) on the surface of the bio-compatible polymeric substrate (P) (I) with, for example a hydrophilic, isocyanate-terminated spacer (II) having at least one isocyanate group at its first and second ends. The resulting product is a bio-compatible polymeric substrate containing isocyanate functionality (III).

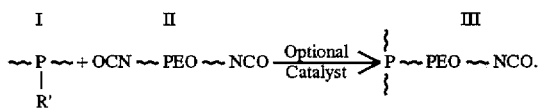

wherein, R' is —OH or —NH$_2$. An optional catalyst may be used to facilitate the above-described reaction, such as for example, dibutyltindilaurate (DBTDL). The product (III) of the reaction indicated above is a bio-compatible polymeric substrate-spacer product. Although the present invention describes the preferred isocyanate terminated spacer, any spacer group can be used which binds to both the bio-compatible polymeric substrate and the bio-active agent of the present invention. A bio-active agent, such as heparin, is then covalently bound to the bio-compatible polymeric substrate-spacer product in the presence of an optional catalyst, such as, for example 1-(3-dimethylaminopropyl)-3-ethylcarbodiimide hydrochloride (EDC), as indicated below:

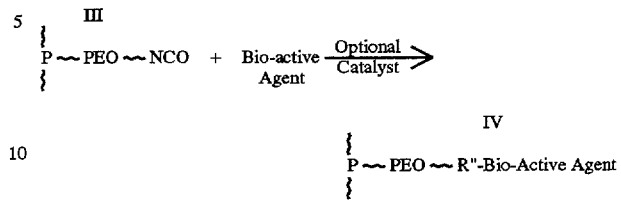

wherein, R" is one of NHCO, NHCOO and NHCONH.

The product (IV) of the reaction indicated above is characterized by the chemical linkage, i.e., R", between the spacer and the bio-active molecule, e.g., heparin. This composition and its method of synthesis will be referred to hereinafter as "Inventive Embodiment I."

Thus, in Inventive Embodiment I, an optional catalyst is used to facilitate the reaction in which the bio-active agent is covalently bound to the bio-compatible polymeric substrate via the hydrophilic isocyanate-terminated spacer. In this reaction, the linkage between the spacer and the bio-active agent is characterized by one of NHCO, NHCOO and NHCONH linkages. Preferably, EDC catalyzes this reaction in the solution of the present invention. In aqueous environments, EDC may function as a dehydrating agent, as well as, a catalyst. In non-aqueous organic solvents, various carbodiimides can be used, such as, for example, dicyclohexyl carbodiimide.

In another embodiment of the present invention, a medical device was prepared by providing a bio-compatible polymeric substrate (P) as described above. The first reaction in this embodiment is identical to the first reaction in Inventive Embodiment I. In particular, the bio-compatible polymeric substrate (V) having reactive functionality, R', on a surface thereof is reacted with a hydrophilic spacer (IV) having at least one reactive functional group at its first and second ends, such as for example an isocyanate terminated spacer. The resulting product is a bio-compatible polymeric substrate containing, for example, isocyanate functionality (VII).

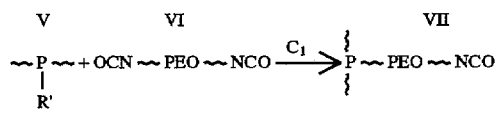

where R' is —OH or —NH$_2$.

The substrate-spacer product (VII) of the reaction indicated above is identical to product (III) of inventive Embodiment I. This substrate-spacer complex is then reacted with an amine terminated (poly)olefin (VIII) having at least one amine group at its first and second ends. Although the preferred amine terminated polyolefin is described, any reactive functional group may be substituted for the amino group on the polyolefin as long as such functional group is capable of binding to the substrate-spacer complex as indicted below.

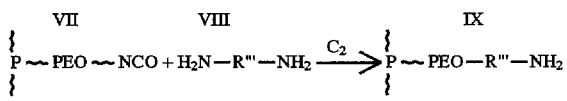

The product (IX) of the reaction indicated above is a polymer-PEO-spacer complex having a chain extending moiety, such as for example, a (poly)olefin having from about 1 to about 1,000 carbon atoms (R'''). This chain extending polyolefin moiety has a reactive functional group, such as for example, an amine group, at its first and second ends. The remaining reactive functional group on the chain extending moiety is capable of covalently bonding to a bio-active agent, such as for example, heparin in the presence of an optional catalyst (e.g., EDC), as indicated below:

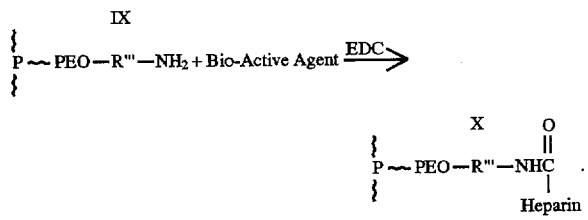

The product (X) of the reaction indicated above is characterized by the chemical linkages between PEO-R''' and R'''-Heparin, respectively. In particular, the chemical link between the PEO spacer and the R''' group is characterized by NHCONH; whereas, the chemical link between the R''' group and the bio-active agent is NHCO. This composition, i.e. product (X), will be referred to hereinafter as "Inventive Embodiment II."

Optional catalysts $C_1$ and $C_2$ may be used to facilitate the indicated reactions. $C_1$ and $C_2$ may be any catalyst capable of driving the indicated reactions. Preferably $C_1$ and $C_2$ are the same catalyst. More preferably, $C_1$ and $C_2$ are dibutyltindilaurate.

Inventive Embodiments I and II significantly improve upon previously described bio-active coating compositions and methods of making same, such as the Park Method described hereinabove. In particular, the method of the present invention provides for approximately a 100% increase in polymer yield, while significantly decreasing the amount of polymer cross-linking, i.e. unwanted side-reactions and cross-reactions, and without sacrificing heparin bio-activity.

The bio-active agent of the present invention is bound either directly (Inventive Embodiment I) or indirectly (Inventive Embodiment II) to a surface of the bio-compatible polymeric substrate via an isocyanate-terminated spacer group. As is clear from the above discussion and structural formulae, the isocyanate group is attached directly to the spacer backbone, as compared to prior art devices wherein the spacer was chain extended with a polyisocyanate. As anyone of ordinary skill in this art would appreciate, the spacers of the instant invention is therefore distinguished from chain-extended prior art spacers in that the former contain no urea or urethane linkages in their backbones. (Stated alternatively, urea or urethane linkages may be present only as terminal residues on the spacer unit due to reaction of a terminally bonded isocyanate group or groups, but not as intervening units). The spacer group may include poly(oxy olefins) (e.g., poly(ethylene oxide)), aliphatic polyesters, polyamino acids, polyamines, hydrophilic polysiloxanes, hydrophilic polysilazanes, hydrophilic acrylates, hydrophilic methacrylates, and linear or lightly branched polysaccharides. The spacer group is intended to be hydrophilic in order to take advantage of the natural repulsive forces of the hydrophobic bio-compatible polymeric substrate. The spacer group should have reactive functional groups on each end that are capable of reacting with and binding to the bio-compatible polymeric substrate and bio-active agent, respectively. Preferably, the reactive functional group on each end of the spacer is, for example, an isocyanate group. An isocyanate end-blocked poly (ethylene oxide) is a preferred example.

Moreover, hydrophilic poly(ethylene oxide) spacers are preferred because they have low interfacial free energy, lack binding sites, and exhibit highly dynamic motion. These characteristics are important because they increase the activity of a PEO-linked bio-active agent, e.g., heparin. See, K. D. Park et al., supra.

The R''' group in Inventive Embodiment II serves to further extend the bio-active agent from the bio-compatible polymer substrate, and to provide a different reaction pathway for binding the bio-active agent to the bio-compatible polymer substrate.

As previously described, the length of the spacer group may be used to control the bio-active agent's activity. It is known in the art that the anti-thrombogenic activity of heparin is increased when it is positioned a certain distance from the substrate to which it is bound. For example, in a comparison of polymeric substrate-spacer-heparin coatings using a $C_6$ alkyl spacer, PEO 200, PEO 1000 and PEO 4000, the polymer-PEO 4000-Heparin surface maintained the highest bio-activity. See, K. D. Park et al., supra. Thus, methods are available in the art for controlling the activity of a polymer-bound bio-active agent. By utilizing such methods, one may determine the optimal length of the spacer. Accordingly, as used herein, "effective distance" means the distance between the bound bio-active agent and the surface of the bio-compatible polymeric substrate which corresponds to a desired level of activity in the bio-active agent.

Thus, in the present invention, control over the bio-active agent's activity is achieved by varying the length, i.e., molecular weight, of the spacer group in Inventive Embodiments I and II and the R''' group in Inventive Embodiment II. The spacer group may have a molecular weight of about 100 to about 200,000 daltons. Preferably, the spacer group has a molecular weight of about 200 to about 50,000 daltons. More preferably, the spacer group has a molecular weight of about 1,000 to about 10,000 daltons. Most preferably, the spacer group has a molecular weight of 4,000 daltons.

In accordance with the present invention, a significant reduction of thrombus formation and/or infection associated with the use of bio-compatible polymeric substrates is achieved by combining an anti-thrombogenic and/or anti-infective agent in a coating to be applied to the host-contacting surface(s) of the bio-compatible polymeric substrate. A variety of anti-infective agents as known in the art may be used, including, antibiotics, such as penicillin and antibacterial agents such as silver sulfadiazine. Similarly, a variety of anti-thrombogenic agents known in the art may be used, including, heparin, aldehyde-terminated heparin, hirudin, prostaglandin, urokinase, streptokinase, sulfated polysaccharide, and albumin. In some cases it may be desirable to provide either dual anti-infective or anti-thrombogenic action with two or more agents. Additionally, it may be desirable to combine an anti-infective and an anti-thrombogenic action by combining two or more of these different agents. The invention is described in terms of the preferred heparin, a known anti-thrombogenic agent of known safety and high anti-coagulation activity, with the understanding that the invention contemplates any anti-thrombogenic and/or anti-infective agent which may be grafted to the bio-compatible polymeric substrate by the method of the present invention.

In another embodiment of the invention, a coating composition for a bio-compatible polymeric substrate is described which includes hydroxyl and/or amine functionality and at least one pendant moiety bonded to the substrate via the hydroxyl and/or amine functionality. Other reactive functionalities may be substituted for the preferred hydroxyl and/or amine as long as such functionality is reactive with the hydrophilic, isocyanate-terminated spacer.

In a further embodiment of the invention, a method for preparing a bio-active coating is described in which a bio-active group is covalently bonded through a hydrophilic spacer group to a hydrophobic, bio-compatible polymeric substrate. The hydrophilic spacer group has at least one reactive functional group at its first and second ends. As described hereinabove, an amine or hydroxyl functionality is introduced onto the surface of the bio-compatible polymeric substrate. Although the preferred amine or hydroxyl functionality is described, any functional group may be used which can participate in bonding a spacer group to the bio-compatible polymeric substrate.

Once the amine and/or hydroxyl containing bio-compatible polymeric substrate is provided, it is reacted with a hydrophilic, spacer as described hereinabove. Upon such a reaction, the spacer is covalently bonded to the bio-compatible polymeric substrate via one of the reactive functional groups on the spacer. As described hereinabove, by further bonding the remaining reactive functional group on the spacer with a bio-active agent in the presence of a catalyst, such as EDC, the bio-active agent is covalently bonded to the spacer.

In yet another embodiment of the invention, a bio-active coating composition includes a bio-compatible polymeric substrate having hydroxyl and/or amine functionality, a hydrophilic spacer having at least one reactive functional group at its first and second ends and a bio-active agent which is covalently reactive with one of the reactive functional groups on the spacer. As used herein, "covalently reactive with" means that the bioactive agent is capable of forming a covalent bond with an unreacted end of the isocyanate terminated spacer.

The invention being thus described, it will be obvious that the same may be varied in many ways. Such variations are not to be regarded as a departure from the spirit and scope of the invention and all such modifications are intended to be included within the scope of the following claims.

What is claimed is:

1. An implantable medical device comprising:
a bio-compatible polymeric substrate surface bonded to a pendent bio-active-containing moiety via the reaction of available functional groups on said substrate with said pendent bio-active-containing moiety, said moiety being represented by the formula:

wherein $R^1$ is a hydrophilic spacer selected from the group consisting of aliphatic hydrocarbons, poly(oxy olefins), hydrophilic polyethers, hydrophilic polyethylenes, polyolefins, aliphatic polyesters, polyamines, polysiloxanes, polysilazanes, hydrophilic acrylates, hydrophilic methacrylates, polyamino acids, and linear polysaccharides; and $R^2$ is a bio-active agent selected from the group consisting of antithrombogenic agents, antibiotics, antibacterial agents, antiviral agents, their pharmaceutical salts and mixtures thereof, which is linked to the carbonyl by O or NH, wherein $R^1$ does not contain urea or urethane linkages in its backbone.

2. The implantable medical device of claim 1, wherein said reactive functional group on said spacer is selected from the group consisting of isocyanate, amine, hydroxyl, carboxyl and mixtures thereof.

3. The implantable medical device of claim 1, wherein said available functional groups of said bio-compatible polymeric substrate surface are selected from the group consisting of hydroxyl, amine, carboxyl and mixtures thereof.

4. The implantable medical device of claim 1, wherein said hydrophilic spacer is an isocyanate end-blocked poly (ethylene oxide).

5. The implantable medical device of claim 4, wherein said isocyanate end-blocked poly(ethylene oxide) has a molecular weight of about 100 daltons to about 200,000 daltons.

6. The implantable medical device of claim 4, wherein said isocyanate end-blocked poly(ethylene oxide) has a molecular weight of about 200 to about 50,000 daltons.

7. The implantable medical device of claim 4, wherein said isocyanate end blocked poly(ethylene oxide) has a molecular weight of about 1,000 to about 4,000 daltons.

8. The implantable medical device of claim 1, wherein the molecular weight of said spacer positions said bio-active agent at an effective distance from said bio-compatible polymeric substrate.

9. The implantable medical device of claim 1, wherein said antithrombogenic agent is selected from the group consisting of heparin, aldehyde-terminated heparin and their pharmaceutical salts.

10. The implantable medical device of claim 1, wherein said bio-compatible polymeric substrate is expanded polytetrafluoroethylene or polyethyleneterephthalate.

11. An implantable medical device having a bio-active coating, said device being prepared by the steps comprising:
a) providing a bio-compatible polymeric substrate having reactive functionality on a surface thereof, and applying said bio-active coating to said surface, wherein said coating is the reaction product of:
i) a first reaction comprising the reaction of said bio-compatible polymeric substrate with a hydrophilic spacer having at least one reactive functional group at its first and second ends, wherein one of said reactive functional groups of said spacer reacts with said reactive functionality on said surface of said bio-compatible polymeric substrate to bond said spacer to said bio-compatible polymeric substrate; and
ii) a second reaction comprising the bonding of a remaining unreacted end of said spacer with a bio-active agent to covalently bond said bio-active agent to said spacer by O or NH which is linked to the carbonyl bond of an amide linkage formed between said spacer and said bio-active agent, and wherein said spacer does not contain urea or urethane linkages in its backbone.

12. The implantable medical device of claim 11, wherein said bio-compatible polymeric substrate is expanded polytetrafluoroethylene or polyethyleneterephthalate.

13. The implantable medical device of claim 11, wherein said hydrophilic spacer is selected from the group consisting of aliphatic hydrocarbons, poly(oxy olefins) hydrophilic polyethers, hydrophilic polyethylenes, polyolefins, aliphatic polyesters, polyamines, polysiloxanes, polysilazanes, hydrophilic acrylates, hydrophilic methacrylates, polyamino acids, and linear polysaccharides.

14. The implantable medical device of claim 11, wherein said reactive functionality on said bio-compatible polymeric substrate is selected from the group consisting of hydroxyl, amine, carboxyl and mixtures thereof.

15. The implantable medical device of claim 11, wherein said reactive functional group of said spacer is selected from the group consisting of isocyanate, amine, hydroxyl, carboxyl and mixtures thereof.

16. The implantable medical device of claim 11, wherein said hydrophilic spacer is an isocyanate end-blocked poly(ethylene oxide).

17. The implantable medical device of claim 16, wherein said isocyanate end-blocked poly(ethylene oxide) has a molecular weight of about 100 daltons to about 200,000 daltons.

18. The implantable medical device of claim 16, wherein said isocyanate end-blocked poly(ethylene oxide) has a molecular weight of about 200 to about 50,000 daltons.

19. The implantable medical device of claim 16, wherein said is ocyanate end-blocked poly(ethylene oxide) has a molecular weight of about 1,000 to about 4,000 daltons.

20. The implantable medical device of claim 11, wherein the molecular weight of said hydrophilic spacer positions said bio-active agent at an effective distance from said bio-compatible polymeric substrate.

21. The implantable medical device of claim 11, wherein said bio-active agent is selected from the group consisting of anti-thrombogenic agents, antibiotic agents, antiviral agents, their pharmaceutical salts and mixtures thereof.

22. The implantable medical device of claim 11, wherein said bio-active agent is selected from the group consisting of heparin, aldehyde-terminated heparin and their pharmaceutical salts.

23. The implantable medical device of claim 11, wherein said second reaction proceeds in the presence of a catalyst.

24. The implantable medical device of claim 23, wherein said catalyst is 1-(3-dimethylaminopropyl)-3-ethylcarbodiimide hydrochloride.

25. An implantable medical device having a bio-active coating, said device being prepared by the steps comprising:

a) providing a bio-compatible polymeric substrate having reactive functionality on a surface thereof, and applying said bio-active coating to said surface, wherein said coating is the reaction product of:

i) a first reaction comprising the reaction of said bio-compatible polymeric substrate with a hydrophilic spacer having at least one reactive functional group at its first and second ends, wherein one of said reactive functional groups on said spacer reacts with said reactive functionality on said bio-compatible polymeric substrate to bond said spacer to said bio-compatible polymeric substrate;

ii) a second reaction comprising the reaction of a chain extending moiety having at least one reactive functional group on its first and second ends with a remaining unreacted end of said spacer, wherein the chain extender is bonded to the spacer by O or NH which is linked to the carbonyl bond of an amide linkage formed between said spacer and said chain extender, and wherein said spacer does not contain urea or urethane linkages in its backbone; and iii) a third reaction comprising the reaction of a remaining unreacted end of said chain extending moiety with a bio-active agent to covalently bond said bio-active agent to said chain extending moiety.

26. The implantable medical device of claims 25 further comprising a catalyst for enhancing said first and second reactions.

27. The implantable medical device of claim 26, wherein said catalyst is dibutyltindilaurate.

28. The implantable medical device of claim 25, wherein said chain extending moiety is a (poly)olefin having from about 1 to about 1000 carbon atoms.

* * * * *

UNITED STATES PATENT AND TRADEMARK OFFICE
CERTIFICATE OF CORRECTION

PATENT NO. : 5,728,751
DATED : March 17, 1998
INVENTOR(S) : Patnaik

It is certified that error appears in the above-identified patent and that said Letters Patent is hereby corrected as shown below:

Column 1, Line 46,      now reads "vital", should read --viral--;

Column 6, Line 23,      now reads "and is nor", should read --and is not--;

IN THE CLAIMS

Claim 19, Column 13, Line 16,      now reads "is ocyanate" should read --isocyanate--.

Signed and Sealed this

Twenty-third Day of June, 1998

Attest:

Attesting Officer

BRUCE LEHMAN

Commissioner of Patents and Trademarks